(12) United States Patent
Lin et al.

(10) Patent No.: US 11,105,763 B2
(45) Date of Patent: Aug. 31, 2021

(54) METHOD FOR MEASURING AN ANALYTE IN A BLOOD SAMPLE AND ANALYTE MEASURING DEVICE

(71) Applicant: HEALTH & LIFE CO., LTD., New Taipei (TW)

(72) Inventors: Meng-Yi Lin, New Taipei (TW); Po-Han Chen, New Taipei (TW); Pei-Chen Chang, New Taipei (TW)

(73) Assignee: HEALTH & LIFE CO., LTD., New Taipei (TW)

( * ) Notice: Subject to any disclaimer, the term of this patent is extended or adjusted under 35 U.S.C. 154(b) by 434 days.

(21) Appl. No.: 16/198,082

(22) Filed: Nov. 21, 2018

(65) Prior Publication Data

US 2019/0204259 A1    Jul. 4, 2019

(30) Foreign Application Priority Data

Dec. 28, 2017    (TW) .................................. 106146172

(51) Int. Cl.
*G01N 27/327*    (2006.01)
*A61B 5/1495*    (2006.01)
*A61B 5/1468*    (2006.01)
*A61B 5/145*     (2006.01)

(52) U.S. Cl.
CPC ....... *G01N 27/3274* (2013.01); *A61B 5/1468* (2013.01); *A61B 5/1495* (2013.01); *A61B 5/14532* (2013.01); *G01N 27/3273* (2013.01)

(58) Field of Classification Search
None
See application file for complete search history.

(56) References Cited

U.S. PATENT DOCUMENTS

2006/0108236 A1 *   5/2006   Kasielke ............ G01N 27/3273
                                                        205/792

FOREIGN PATENT DOCUMENTS

WO    WO-2012012135 A2 *   1/2012   ......... A61B 5/14532

* cited by examiner

*Primary Examiner* — J. Christopher Ball
(74) *Attorney, Agent, or Firm* — Hamre, Schumann, Mueller & Larson, P.C.

(57) ABSTRACT

A method includes steps of: applying a first voltage signal on a blood sample so as to obtain a preliminary value regarding an analyte in the blood sample; applying on the blood sample, a second voltage signal that includes cycles of a pulse and that has a voltage value alternating between high and low levels; measuring a physical quantity resulting from application of the second voltage signal on the blood sample at a time point in one of the cycles of the pulse of the second voltage signal so as to generate a calibration value; and calibrating the preliminary value based on the calibration value so as to obtain a calibrated value of the analyte in the blood sample which serves as a result of measurement of the analyte.

16 Claims, 12 Drawing Sheets

METHOD FOR MEASURING AN ANALYTE IN A BLOOD SAMPLE AND ANALYTE MEASURING DEVICE

CROSS-REFERENCE TO RELATED APPLICATION

This application claims priority of Taiwanese Invention Patent Application No. 106146172, filed on Dec. 28, 2017.

FIELD

The disclosure relates to a method for measuring an analyte in a blood sample, and more particularly to a method for measuring an analyte in a blood sample by applying a voltage signal on the blood sample. The disclosure further relates to an analyte measuring device adapted to measure an analyte in a blood sample.

BACKGROUND

A conventional method for measuring blood sugar (i.e., glucose) in a blood sample includes steps of: adding an enzyme to the blood sample, so that the enzyme reacts with glucose in the blood sample to result in an intermediate, which further reacts with an electron transfer substance to result in electrons accumulated on a surface of an electrode; and applying a direct current (DC) voltage signal on the electrode so as to result in an electric current. Since a magnitude of the electric current is substantially proportional to a concentration of the glucose in the blood sample, the concentration of the glucose in the blood sample can be determined by measuring the magnitude of the electric current.

However, a result of measurement of blood sugar (or other analyte) in a blood sample is influenced by factors such as the hematocrit (HCT), which represents the volume percentage of red blood cells in the blood sample. A reaction rate between the added enzyme and the glucose in a blood sample with high HCT is lower than that in a blood sample with normal HCT, and so is a reaction rate between the intermediate and the electron transfer substance, so for a blood sample with high HCT, relatively less electrons are accumulated on the surface of the electrode and relatively low electric current is generated. Therefore, the blood sugar concentration in a blood sample with high HCT may be underestimated. On the other hand, the blood sugar concentration in a blood sample with low HCT may be overestimated. Inaccuracy of the result of blood sugar measurement may mislead clinical practitioners and the accuracy of the result of blood sugar measurement needs to be improved upon.

SUMMARY

Therefore, an object of the disclosure is to provide a method for measuring an analyte in a blood sample and an analyte measuring device adapted to measure an analyte in a blood sample that can alleviate at least one of the drawbacks of the prior art.

According to one aspect of the disclosure, the method is to be implemented by an analyte measuring device. The method includes steps of:

applying, by the analyte measuring device, a first voltage signal on the blood sample so as to obtain a preliminary value regarding the analyte in the blood sample based on a measured physical quantity resulting from application of the first voltage signal;

applying, by the analyte measuring device on the blood sample, a second voltage signal that includes N number of cycles of a pulse and that has a voltage value alternating between high and low levels, where N is an integer not smaller than two;

measuring, by the analyte measuring device, a physical quantity resulting from application of the second voltage signal on the blood sample at a time point in one of the cycles of the pulse of the second voltage signal so as to generate a calibration value based on the physical quantity measured at the time point; and calibrating, by the analyte measuring device based on the calibration value, the preliminary value of the analyte in the blood sample so as to obtain a calibrated value of the analyte in the blood sample which serves as a result of measurement of the analyte.

According to another aspect of the disclosure, the analyte measuring device includes an electrode unit, a sensor, and a processor. The electrode unit is to be in contact with the blood sample. The sensor is connected to the electrode unit. The processor is connected to the electrode unit and the sensor. The processor is configured to apply a first voltage signal on the blood sample via the electrode unit, and to read from the sensor a measured physical quantity that results from application of the first voltage signal so as to obtain a preliminary value regarding the analyte in the blood sample based on the measured physical quantity. The processor is configured to apply, via the electrode unit on the blood sample, a second voltage signal that includes N number of cycles of a pulse and that has a voltage value alternating between high and low levels, where N is an integer not smaller than two. The processor is configured to measure, via said sensor, the physical quantity resulting from application of the second voltage signal on the blood sample at a time point in one of the cycles of the pulse of the second voltage signal so as to generate a calibration value based on the physical quantity measured at the time point. The processor is configured to calibrate, based on the calibration value, the preliminary value of the analyte in the blood sample so as to obtain a calibrated value of the analyte in the blood sample which serves as a result of measurement of the analyte.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
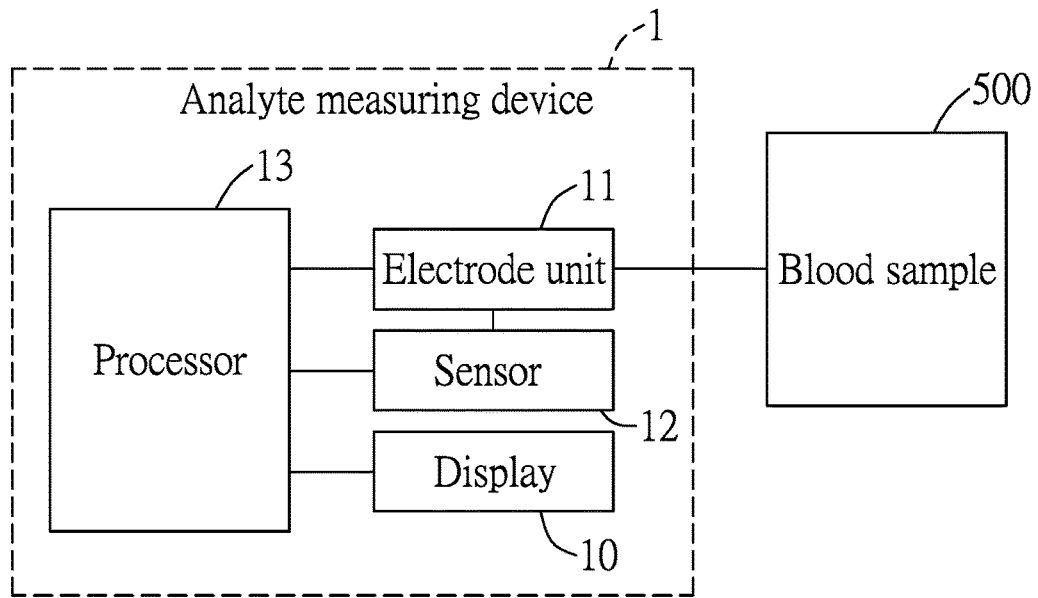
FIGS. 1 and 13 are block diagrams illustrating an embodiment of an analyte measuring device adapted to measure an analyte in a blood sample according to the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIG. 1, an embodiment of an analyte measuring device 1 adapted to measure an analyte in a blood sample 500 is illustrated. In this embodiment, the analyte is implemented to be blood sugar (i.e., glucose), but implementation thereof is not limited thereto and may vary in other embodiments. The analyte measuring device 1 includes a display 10, an electrode unit 11, a sensor 12 connected to the electrode unit 11, and a processor 13 connected to the display 10, the electrode unit 11 and the sensor 12.

Figure 13:
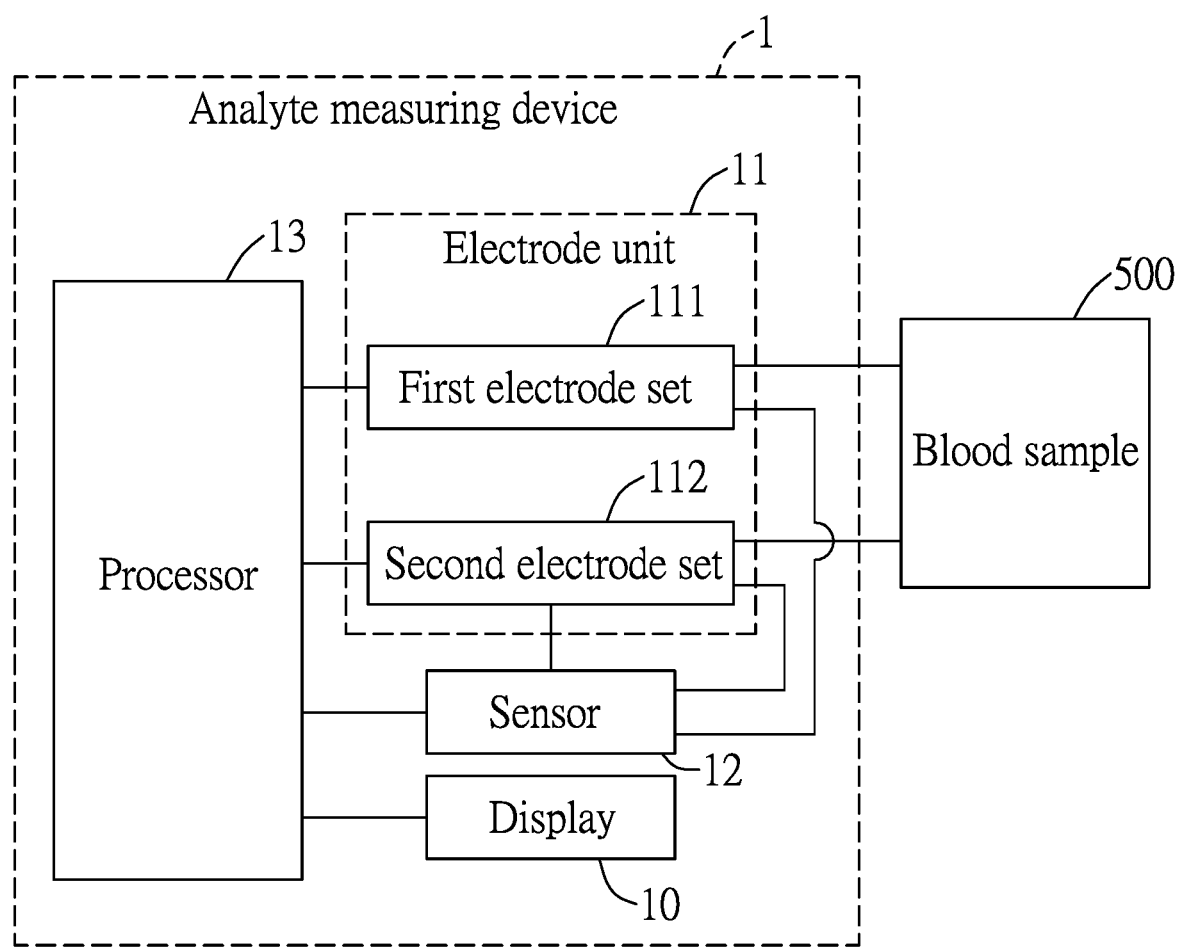

As shown in FIG. 13, the electrode unit 11 is to be in contact with the blood sample 500. In this embodiment, the electrode unit 11 includes a first electrode set 111 and a second electrode set 112 each of which has a positive terminal and a negative terminal. However, implementation of the electrode unit 11 is not limited to what is disclosed herein and may vary in other embodiments. For example, the electrode unit 11 may include only one electrode set in some embodiments. In this embodiment, the first electrode set 111 is to be connected between the processor 13 and the blood sample 500, and the second electrode set 112 is to be connected between the processor 13 and the blood sample 500 as well.

The sensor 12 is configured to measure a physical quantity resulting from application of one of a first voltage signal and a second voltage signal on the blood sample 500. In this embodiment, the sensor 12 includes a current meter (not shown), and the measured physical quantity is implemented to be a value of electric current, but implementation of the measured physical quantity is not limited thereto and may vary in other embodiments.

The processor 13 is configured to apply the first voltage signal on the blood sample 500 via the electrode unit 11 and read, from the sensor 12, the measured physical quantity that results from application of the first voltage signal so as to obtain a preliminary value regarding the analyte in the blood sample 500 based on the measured physical quantity. In this embodiments, the preliminary value is implemented to be a blood sugar concentration (i.e., blood glucose level), but implementation thereof is not limited thereto and may vary in other embodiments. Specifically speaking, the blood sugar concentration is determined based on a predetermined mapping rule associated with a correspondence relationship between the blood sugar concentration and the value of electric current.

In addition, the processor 13 is configured to apply, via the electrode unit 11 on the blood sample 500, the second voltage signal that includes N number of cycles of a pulse and that has a voltage value alternating between high and low levels, where N is an integer not smaller than two. In one embodiment, the processor 13 is configured to apply the first voltage signal on the blood sample 500 via one of the first and second electrode sets 111 and 112, and apply the second voltage signal on the blood sample 500 via the other one of the first and second electrode sets 111 and 112. However, implementation of applying the first voltage signal and the second voltage signal is not limited to what is disclosed herein and may vary in other embodiments. For example, the processor 13 may be configured to apply both the first voltage signal and the second voltage signal on the blood sample 500 via an identical one of the first and second electrode sets 111 and 112.

The processor 13 is configured to then measure, via the sensor 12, the physical quantity resulting from application of the second voltage signal on the blood sample 500, at a time point in one of the cycles of the pulse of the second voltage signal so as to generate a calibration value based on the physical quantity measured at the time point. In one embodiment, the calibration value is generated based on a lookup table associated with correspondence relationship between the calibration value and the physical quantity measured at the time point, but implementation of determining the calibration value is not limited thereto. In one embodiment, the processor 13 is configured to measure, via the sensor 12, the physical quantity at the time point in a K-th one of the cycles of the pulse of the second voltage signal, where K is an integer not smaller than two and not greater than N. In one embodiment, the processor 13 is configured to measure, via the sensor 12, the physical quantity at the time point in each of P number of cycles selected from the cycles of the pulse of the second voltage signal so as to generate calibration values that correspond respectively to the P number of cycles, where P is an integer not smaller than two and not greater than N.

Eventually, the processor 13 is configured to calibrate the preliminary value of the analyte in the blood sample 500 based on the calibration value(s) so as to obtain a calibrated value of the analyte in the blood sample 500 which serves as an accurate result of measurement of the analyte.

Figure 2:
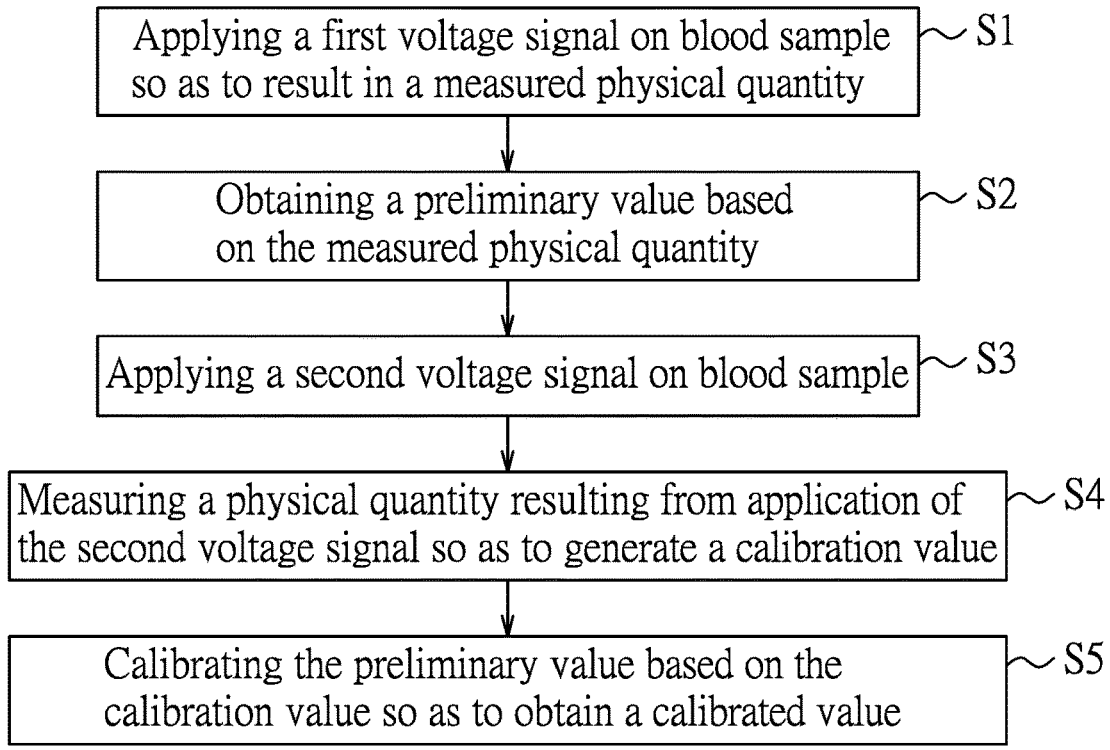
FIG. 2 is a flow chart illustrating a first embodiment of a method for measuring the analyte in the blood sample according to the disclosure.

Referring to FIG. 2, a first embodiment of a method for measuring the analyte in the blood sample 500 is illustrated. The method is to be implemented by the analyte measuring device 1 that is previously mentioned. The method includes steps S1 to S5 that are described as follows.

Figure 3:
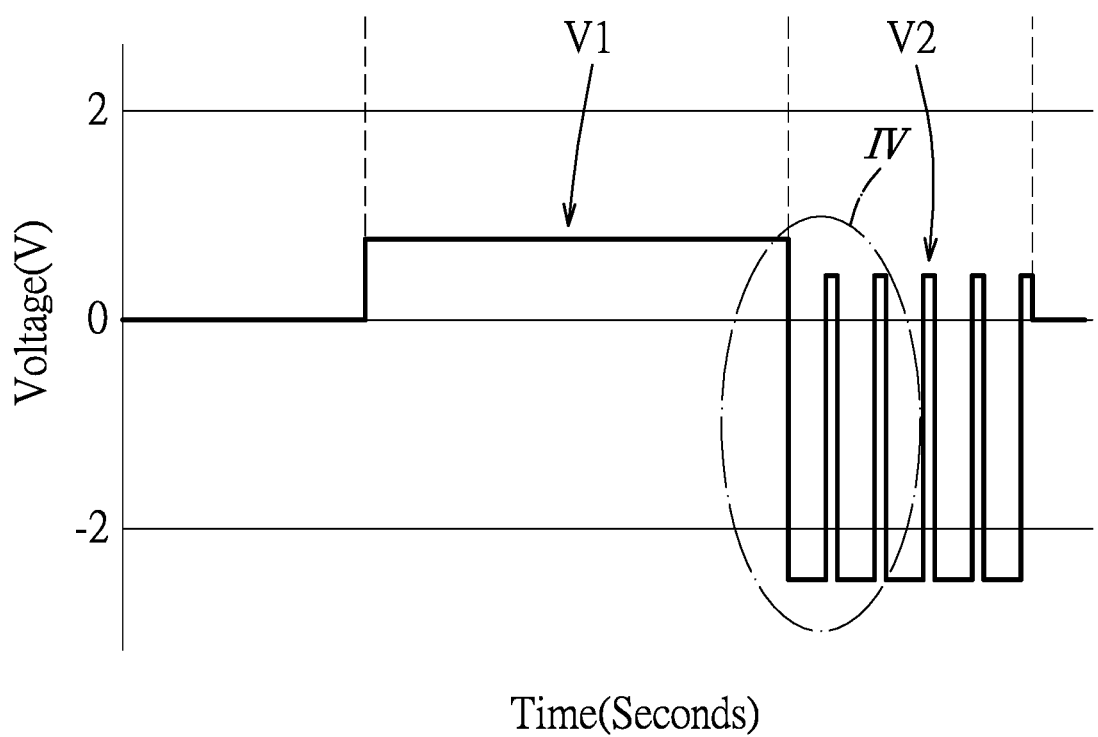
FIG. 3 is a plot illustrating embodiments of a first voltage signal and a second voltage signal utilized in the method according to the disclosure.

In step S1, the analyte measuring device 1 applies the first voltage signal (V1) as shown in FIG. 3 on the blood sample 500 so as to release electrons from the blood sample 500 to result in electric current that is to be sensed by the sensor 12. In one embodiment, the analyte measuring device 1 applies, via the first electrode set 111 on the blood sample 500, a direct current (DC) voltage signal that serves as the first voltage signal, that is positive in polarity and that has a constant voltage value. More specifically, the first voltage signal is 0.4 volts in voltage value and lasts for 5.5 seconds. However, implementation of the first voltage signal is not limited to what is disclosed herein and may vary in other embodiments.

In step S2, the analyte measuring device 1 obtains the preliminary value (i.e., the blood sugar concentration or blood glucose level) regarding the analyte in the blood sample 500 based on the measured physical quantity (i.e., the value of electric current) resulting from application of the first voltage signal. In this embodiment, the processing unit 13 reads the measured physical quantity from the sensor 12 in the period between 5 and 5.5 seconds after the moment the first voltage signal (V1) is applied on the blood sample 500. It should be noted that implementation of when to read the measured physical quantity from the sensor 12 is not limited to what is disclosed herein and may vary in other embodiments.

It is worth to note that, the preliminary value (i.e., the blood sugar concentration or blood glucose level) thus obtained in step S2 is determined without giving consideration to the influence of the hematocrit (HCT) of the blood sample 500 on the measurement of blood sugar, and consequently may deviate from the actual value of the blood sugar concentration. Specifically speaking, for a blood sample of a normal person, the HCT thereof is about 40%. When the HCT of the blood sample 500 is higher than 40%, the blood sugar concentration thus obtained in step S2 will be underestimated. Otherwise, when the HCT of the blood sample 500 is lower than 40%, the blood sugar concentration thus obtained in step S2 will be overestimated. That is to say, the preliminary value cannot precisely represent the actual value of the blood sugar concentration when the influence of the HCT of the blood sample 500 on the measurement of blood sugar is not taken into account.

Figure 4:
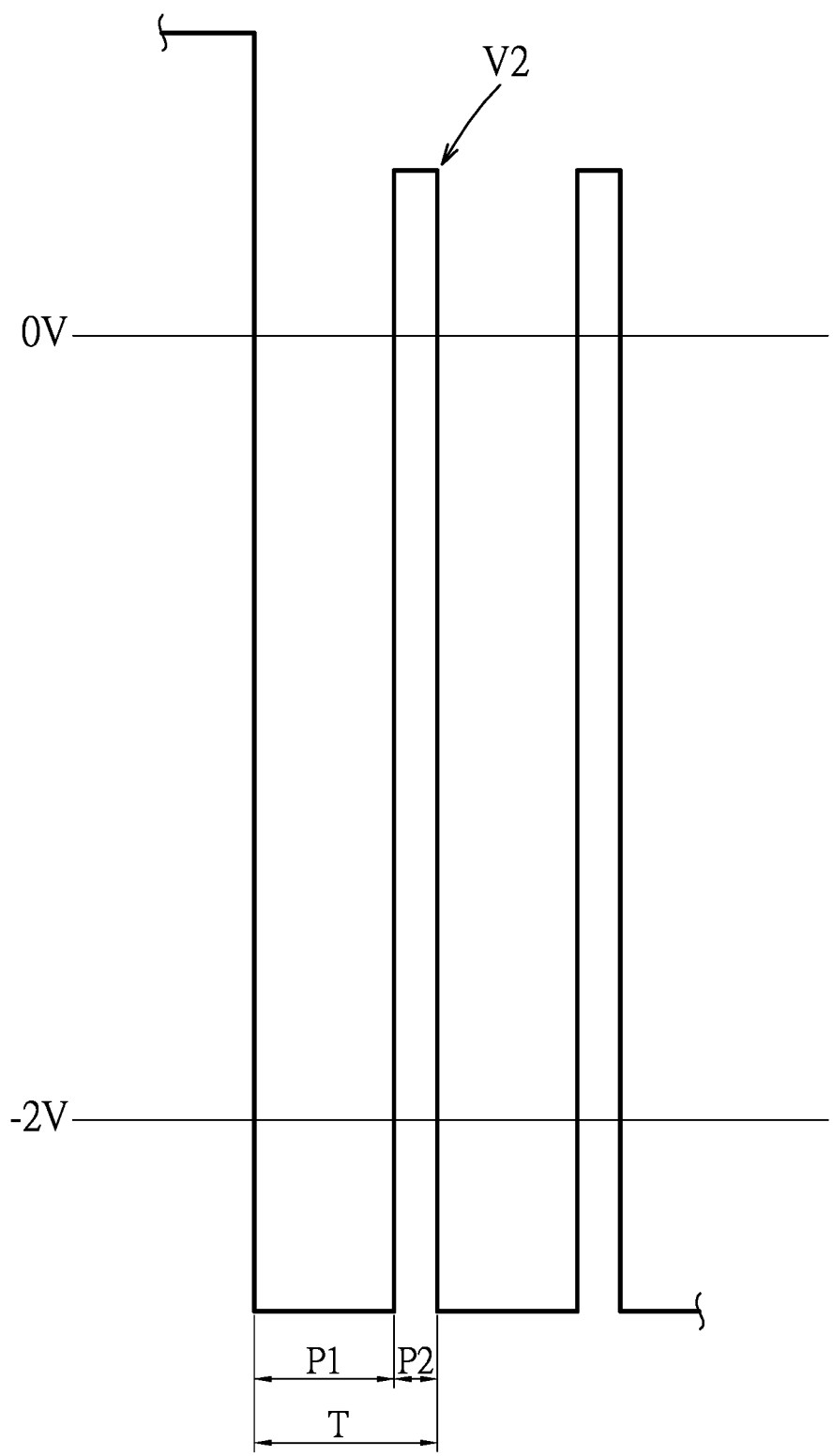
FIG. 4 is a plot illustrating first two cycles of a pulse of the embodiment of the second voltage signal.

In step S3, referring FIGS. 1 and 3 again, the analyte measuring device 1 applies, on the blood sample 500, the second voltage signal (V2) that includes N number of cycles of a pulse and that has a voltage value alternating between high and low levels, where N is an integer not smaller than two. In this embodiment, the analyte measuring device 1 applies, via the second electrode set 112 on the blood sample 500, the second voltage signal (V2) that includes five cycles of the pulse (i.e., N is equal to five, but implementation of the number of the cycles is not limited to what is disclosed herein) and that has the voltage value alternating between the high level that is positive (hereinafter referred to as the positive high level) and the low level that is negative (herein after referred to as the negative low level). Specifically speaking, referring to FIG. 4, each of the cycles of the pulse of the second voltage signal (V2) has a first period (P1) that corresponds to the negative low level, and a second period (P2) that is subsequent to the first period and that corresponds to the positive high level. Moreover, for each of the cycles of the pulse of the second voltage signal (V2), an absolute value of the negative low level corresponding to the first period (P1) in the cycle is different from an absolute value of the positive high level corresponding to the second period (P2) in the cycle, and a length of the first period (P1) in the cycle is different from a length of the second period (P2) in the cycle. In this embodiment, for each of the cycles of the pulse of the second voltage signal (V2), the voltage value of the second voltage signal (V2) is −2.5 volts in the first period (P1), the length of which is 0.3 seconds, and the voltage value of the second voltage signal (V2) is 0.2 volts in the second period (P2), the length of which is 0.1 seconds. However, implementation of the second voltage signal (V2) is not limited to what is disclosed herein and may vary in other embodiments.

In one embodiment, for each of the cycles of the pulse of the second voltage signal (V2), the pulse has the first period (P1) that corresponds to the positive high level, and the second period (P2) that is subsequent to the first period (P1) and that corresponds to the negative low level, while the first voltage signal (V1) is negative in polarity. In other words, the second voltage signal (V2) in the first period (P1) and the first voltage signal (V1) are opposite in polarity. However, in other embodiments, the second voltage signal (V2) in the first period (P1) and the first voltage signal (V1) may be identical in polarity, and implementations thereof are not limited to what are disclosed herein.

In one embodiment, the voltage value of the second voltage signal (V2) may be implemented to alternate between two non-negative levels. For example, the voltage value of the second voltage signal (V2) alternates between 0 volt and 2.5 volts. That is to say, the voltage value of the second voltage signal (V2) is 0 volts in one of the first period (P1) and the second period (P2), and 2.5 volts in the other of the first period (P1) and the second period (P2).

In step S4, the analyte measuring device 1 measures the physical quantity (e.g., the electrical current) resulting from application of the second voltage signal (V2) on the blood sample 500 at a time point in one of the cycles of the pulse of the second voltage signal (V2) so as to generate a calibration value based on the physical quantity measured at the time point. Specifically speaking, the analyte measuring device 1 measures the physical quantity at the time point in a K-th one of the cycles of the pulse of the second voltage signal (V2), where K is an integer not smaller than two and not greater than N. In one embodiment where the second voltage signal (V2) includes five cycles of the pulse, the analyte measuring device 1 measures the physical quantity at the time point at which the first period (P1) in the fifth one of the cycles begins. Alternatively, the processor 13 may read the physical quantity measured by the sensor 12 at a time point in the second period (P2) in the K-th one of the cycles of the pulse of the second voltage signal (V2). The calibration value is to be utilized by the processor 13 to calibrate the preliminary value of the analyte in the blood sample 500 by using the calibration value to compensate deviation between the preliminary value and the actual value of the blood sugar concentration attributed to HCT of the blood sample 500. It should be noted that measuring at the beginning of one cycle of the pulse is beneficial to the determination of the calibration value in terms of accuracy, and a reason will be explained by an experiment shown in the following paragraph.

Figure 5:
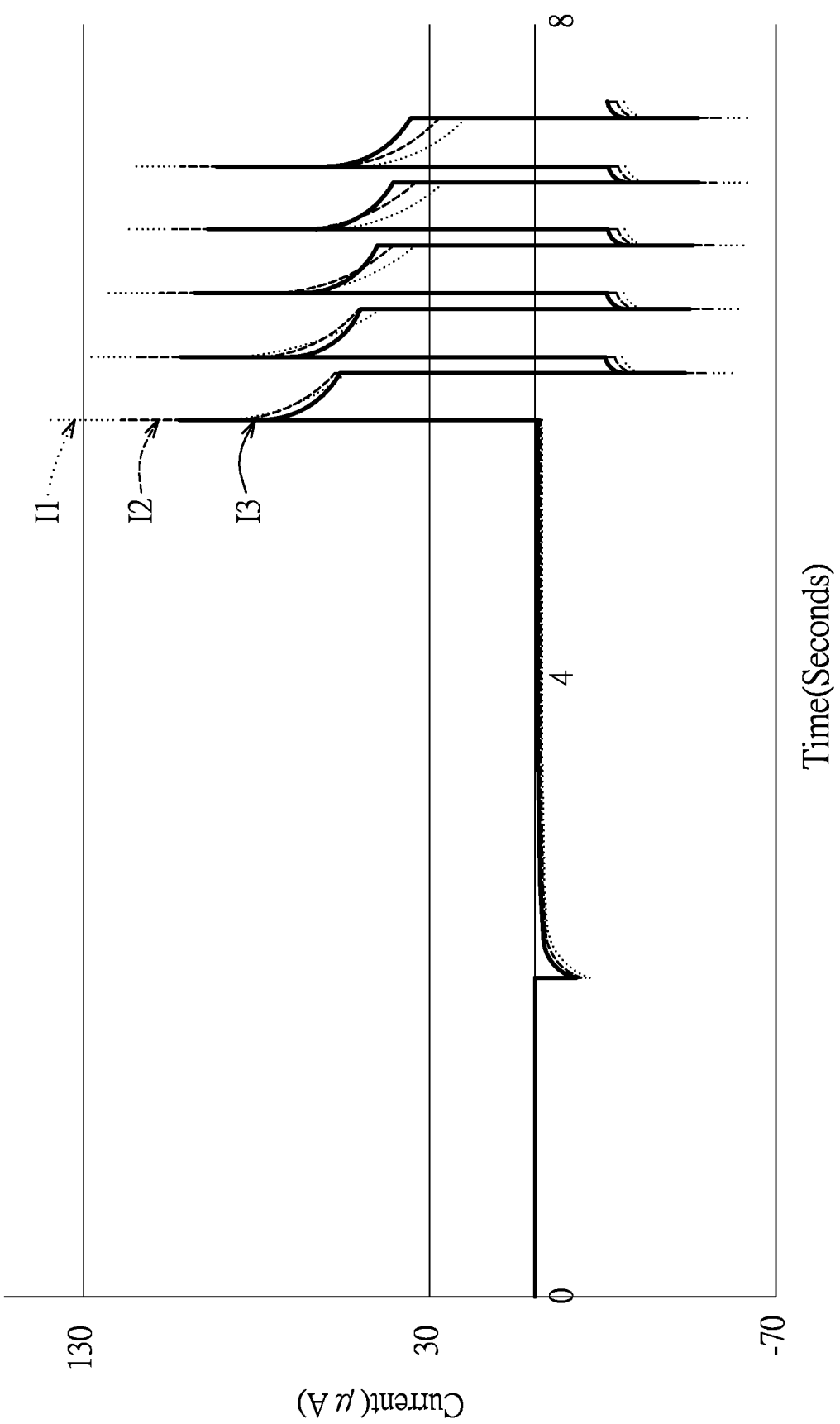
FIG. 5 is a plot illustrating examples of three electric currents resulting from applying the first and second voltage signals on blood samples respectively with three different hematocrits (HCTs)

In the experiment, first, second and third blood samples having HCTs of 20%, 40% and 60%, respectively, were under test. Waveforms of electric currents in FIG. 5 indicate a first electric current (I1), a second electric current (I2) and a third electric current (I3) resulting from application of the first voltage signal (V1) and the second voltage signal (V2) on the first, second and third blood samples, respectively.

Figure 6:
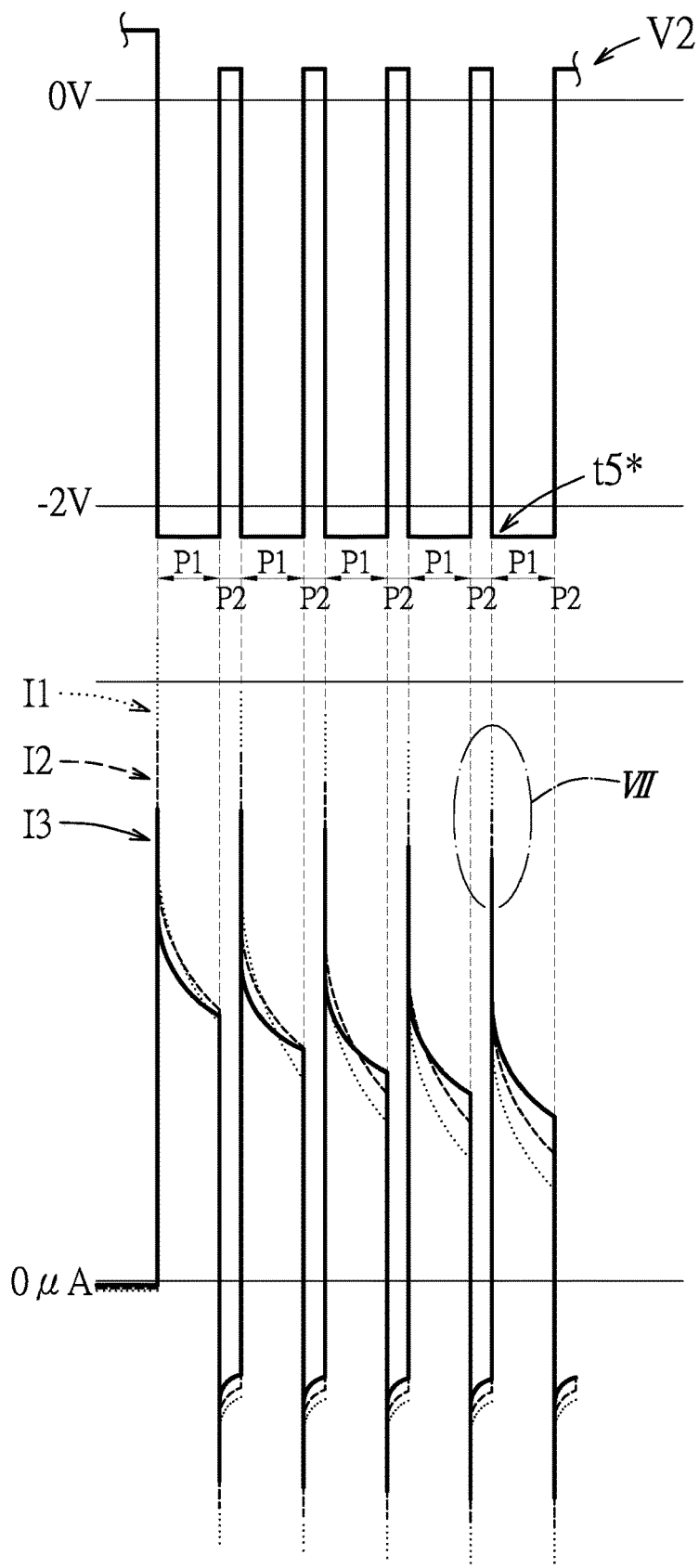
FIG. 6 is a plot illustrating examples of the three electric currents resulting from applying the second voltage signal on the blood samples respectively with three different HCTs in the embodiment of the method.
Figure 7:
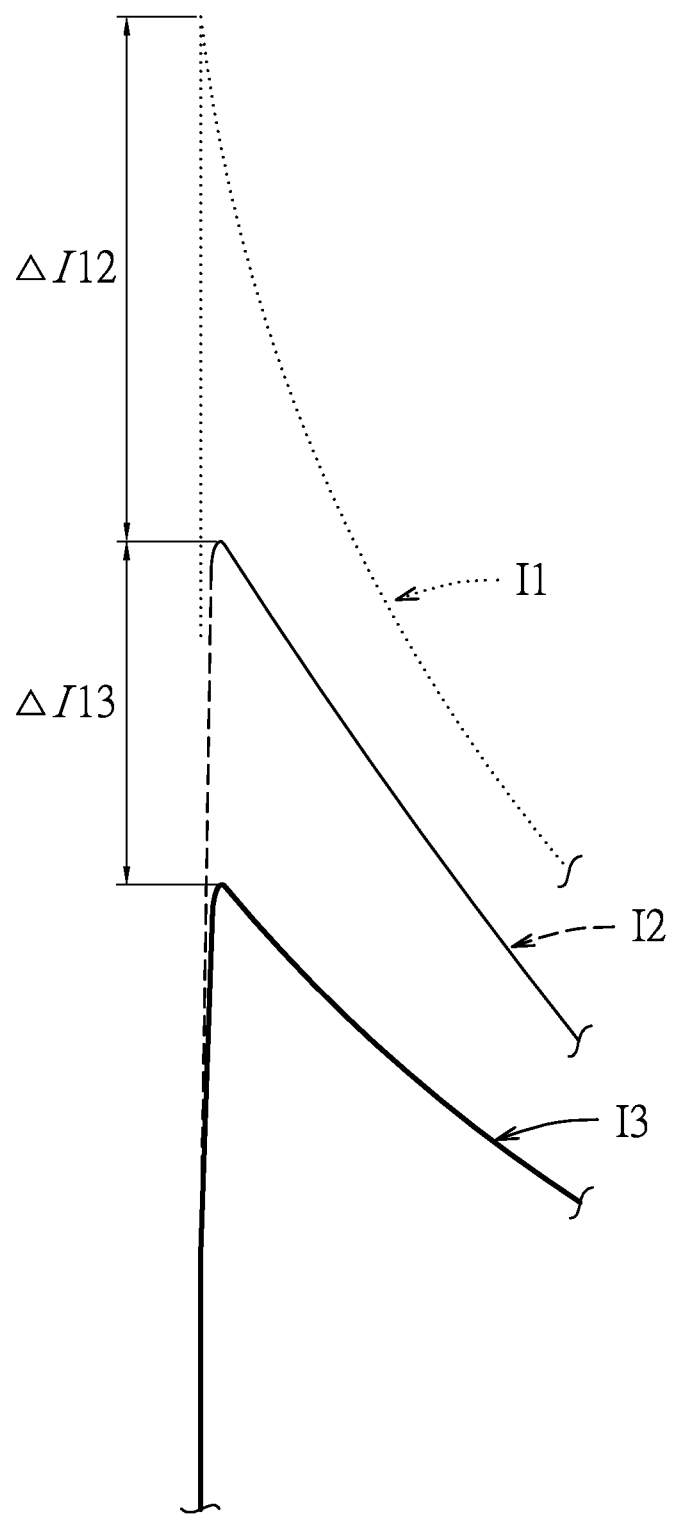
FIG. 7 is a plot illustrating the examples of the three electric currents resulting from applying the second voltage signal on the blood samples respectively with three different HCTs in the embodiment of the method.

Referring to the upper diagram in FIG. 6, around the beginning (which is indicated by "t5*") of the first period (P1) in the fifth cycle of the pulse of the second voltage signal (V2), i.e., around the boundary between the second period (P2) in the fourth cycle and the first period (P1) in the fifth cycle, an instantaneous switching of the voltage signal (V2) from the positive high level to the negative low level caused positive spikes in the first electric current (I1), the second electric current (I2) and the third electric current (I3) as shown in the lower diagram of FIG. 6. FIG. 7 illustrates a fragmentary enlarged diagram of the positive spikes in the first electric current (I1), the second electric current (I2) and the third electric current (I3). Magnitude differences, attributed to differences of the HCTs of the blood samples, between the first and second electric currents (denoted by "ΔI12" in FIG. 7) and between the second and third electric currents (denoted by "ΔI23" in FIG. 7) are the greatest around the beginning of the first period (P1) in the fifth cycle of the pulse of the second voltage signal (V2), and then decrease over time in the first period (P1). Therefore, measuring at the beginning of one cycle of the pulse helps generate the calibration value that faithfully reflects the influence of the HCT of the blood sample on the measurement of the physical quantity.

It is worth to note that implementation of the time point for measuring the physical quantity is not limited to what are disclosed herein and may vary in other embodiments. In one embodiment, the analyte measuring device 1 measures the physical quantity multiple times (e.g., twice) in the K-th one of the cycles of the pulse of the second voltage signal (V2). When there are two measured values of the physical quantity corresponding to a same cycle, a ratio or a difference therebetween (i.e., one of the measured values divided by the other of the measured values, or one of the measured values subtracted from the other of the measured values) may be utilized to generate the calibration value. When there are two or more measured values of the physical quantity, an average or a weighted summation thereof may be utilized to generate the calibration value. It should be noted that implementation of how to obtain the calibration value is not limited to what are disclosed herein.

In step S5, based on the calibration value, the analyte measuring device 1 calibrates the preliminary value of the analyte in the blood sample 500 so as to obtain the calibrated value of the analyte in the blood sample 500 which serves as the result of measurement of the analyte. In this embodiment, the calibrated value of the analyte in the blood sample 500 is implemented to be a calibrated value of blood sugar concentration, and the processor 13 is configured to control the display 10 to display the same. However, implementation of the calibrated value of the analyte in the blood sample 500 is not limited to what is disclosed herein and may vary in other embodiments.

In this embodiment, the calibration value generated in step S4 is 20% (i.e., the HCT of the blood sample 500 is 20%). The processor 13 is configured to obtain the calibrated value of blood sugar concentration by multiplying the preliminary value of the analyte in the blood sample 500 with a predetermined percentage that corresponds to the calibration value. However, implementation of calculating the calibrated value of the analyte in the blood sample 500 is not limited to what is disclosed herein and may vary in other embodiments. To compensate overestimation of the preliminary value of the analyte in the blood sample 500 that results from a relatively lower HCT (e.g., lower than 40%) of the blood sample 500, the predetermined percentage needs to have a relatively lower value. On the other hand, to compensate underestimation of the preliminary value of the analyte in the blood sample 500 that results from a relatively higher HCT (e.g., higher than 40%) of the blood sample 500, the predetermined percentage needs to have a relatively higher value. For example, for a calibration value of 20%, the predetermined percentage corresponding thereto may be 30%; and for a calibration value of 60% (i.e., the HCT of the blood sample 500 is 60%), the predetermined percentage corresponding thereto may be 125%. A lookup table may be utilized to record correspondence relationship between the calibration value and the predetermined percentage.

A second embodiment of the method according to the disclosure is similar to the previous embodiment, with the differences therefrom described as follows. In step S4, the processor 13 of the analyte measuring device 1 measures the physical quantity at the time point at which the first period (P1) in the fifth one of the cycles of the pulse of the second voltage signal (V2) ends. It is worth to note that measuring at the end of one cycle of the pulse is also beneficial to the determination of the calibration value in terms of accuracy. This point will be proven by experiment shown in the following paragraphs.

Figure 8:
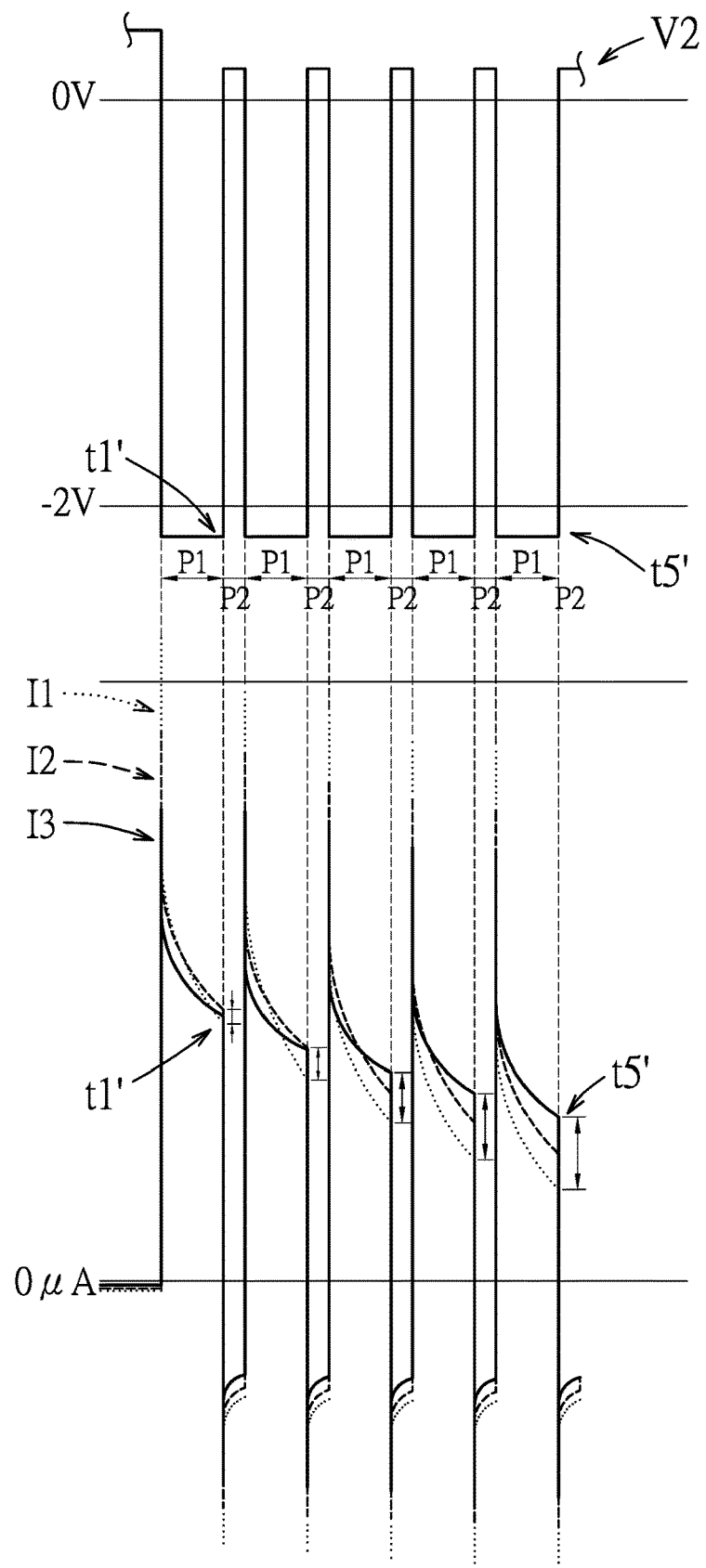
FIG. 8 is a plot illustrating examples of the three electric currents resulting from applying the second voltage signal on blood samples respectively with three different HCTs in a second embodiment of the method.

In the experiment, the first, second and third blood samples having the HCTs of 20%, 40% and 60%, respectively, were under test again. Waveforms of electric currents in FIG. 8 indicate the first electric current (I1), the second electric current (I2) and the third electric current (I3) resulting from applying the second voltage signal (V2) on the first, second and third blood samples, respectively. Referring to the upper diagram in FIG. 8, around the end (which is indicated by "t1'") of the first period (P1) in the first cycle of the pulse of the second voltage signal (V2), decreasing in magnitude of the first electric current (I1), the second electric current (I2) and the third electric current (I3) slows down as shown in the lower diagram of FIG. 8. Magnitudes of the first, second and third electric currents (I1, I2 and I3) are not significantly different from one another around the end of the first period (P1) in the first cycle of the pulse of the second voltage signal (V2). That is to say, measuring at the end of the first period (P1) in the first cycle of the pulse of the second voltage signal (V2) does not help generate the calibration value that faithfully reflects the influence of the HCT of the blood sample on the measurement of the physical quantity. However, under the influence of the second to fifth cycles of the pulse of the second voltage signal (V2) that alternates between the positive high level and the negative low level, the magnitudes of the first, second and third electric currents (I1, I2 and I3) around the end of the first period (P1) diverge increasingly more significantly from the second to fifth cycles of the pulse of the second voltage signal (V2). Referring to the lower diagram in FIG. 8, around the end (which is indicated by "t5'") of the first period (P1) in the fifth cycle of the pulse of the second voltage signal (V2), the magnitude differences among the first, second and third electric currents (I1, I2 and I3) are significant enough to distinguish the differences between the HCTs of the blood samples. Moreover, it should be worth noting that the second voltage signal (V2) is less sensitive to noise around the end of the first period (P1) than around the beginning of the first period (P1) in each cycle of the pulse of the second voltage signal (V2). Consequently, for each of the cycles of the pulse of the second voltage signal (V2), measuring at the end of the first period (P1) is proven to be adequate.

Another experiment is given to show that the amplitude difference between the first electric current (I1) and the third electric current (I3) indeed results from the difference between the HCTs of the blood samples. As shown in the following table, nine blood sample groups utilized in said another experiment are characterized respectively by nine combinations of one of three different levels of HCT (20%, 40% and 60%) and one of three different levels of blood sugar concentration (80 mg/dL, 150 mg/dL and 350 mg/dL), and each of the blood sample groups includes five blood samples. In other words, there are forty five blood samples in total.

| Group No. | HCT (%) | Blood sugar concentration (mg/dL) | Number of blood samples |
|---|---|---|---|
| 1 | 20 | 80 | 5 |
| 2 | 20 | 180 | 5 |
| 3 | 20 | 350 | 5 |
| 4 | 40 | 80 | 5 |
| 5 | 40 | 180 | 5 |
| 6 | 40 | 350 | 5 |
| 7 | 60 | 80 | 5 |
| 8 | 60 | 180 | 5 |
| 9 | 60 | 350 | 5 |

Total number of blood samples: 45

Figure 9:
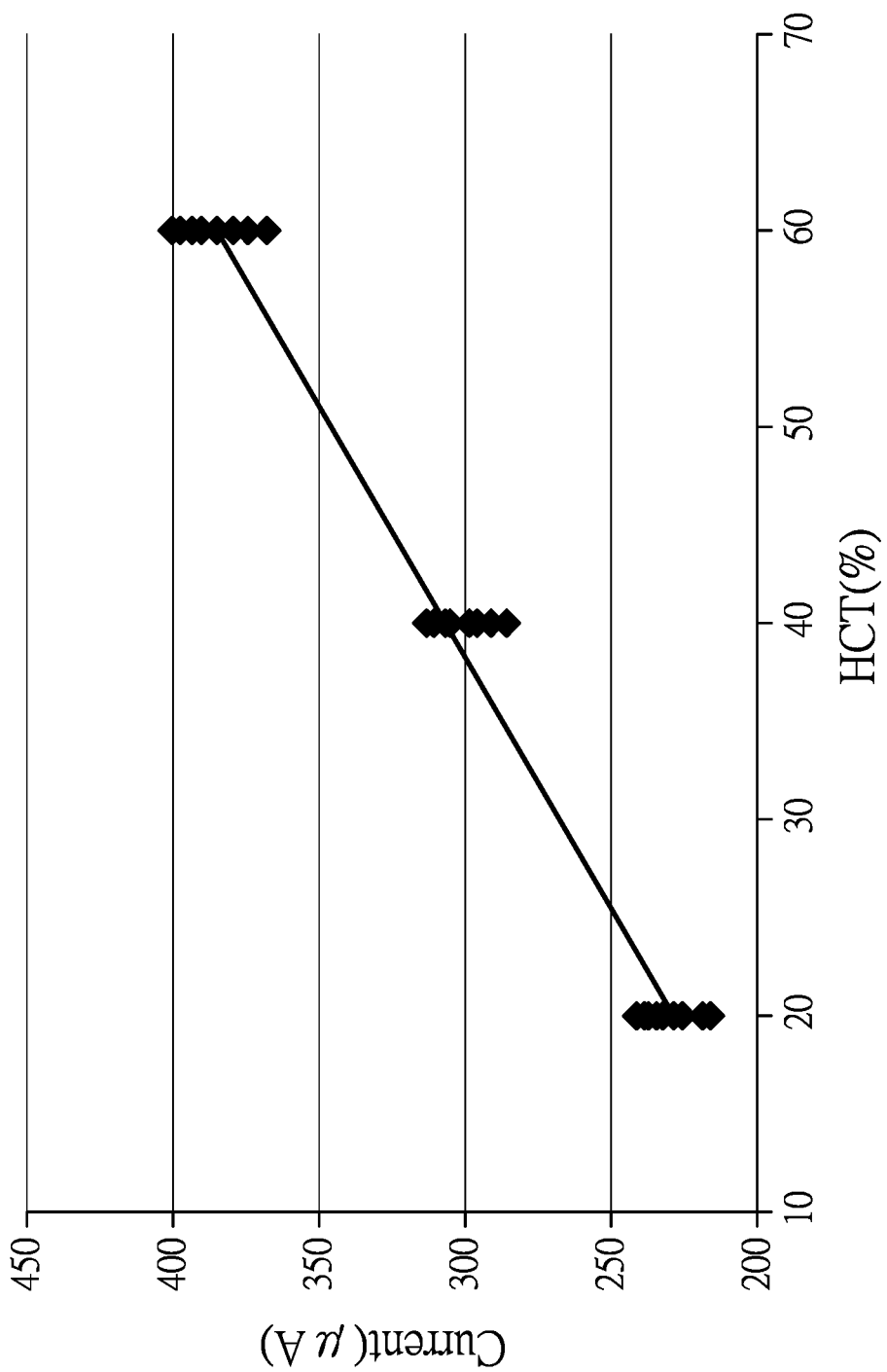
FIG. 9 is a scatter plot illustrating an example of values of electric currents that result from applying the second voltage signal on blood samples with three different HCTs in said second embodiment of the method and that are sampled in a fifth cycle of a pulse of the second voltage signal.

The analyte measuring device 1 applied the second voltage signal (V2) on the blood samples in the nine blood sample groups, and measured, at the time point at which the first period (P1) in the fifth one of the cycles ended, electric currents resulting from the application of the second voltage signal (V2), so as to obtain forty five sample points in total. The sample points corresponding to respective results of measurement of the electric currents are plotted in FIG. 9, where the vertical axis represents magnitude of the electric current thus measured, and the horizontal axis represents the HCT of the blood sample. FIG. 9 demonstrates concentration of values of the electric currents resulting from application of the second voltage signal (V2) on the blood samples with the same HCT. For example, values of the electric currents resulting from application of the second voltage signal (V2) on the blood samples with 20% HCT range roughly between 210 µA and 250 µA; in other words, these values are concentrated within a range of 40 µA. Moreover, three sets of the sample points corresponding to the blood samples that respectively have the HCTs of 20%, 40% and 60% are linearly distributed (see the slope line in FIG. 9). That is to say, the values of the electric currents resulting from application of the second voltage signal (V2) and the HCTs of the blood samples have a linear relationship, and more specifically, are in direct proportion. As a result, measuring the physical quantity at the time point at which the first period (P1) in the fifth one of the cycles ends helps generate the calibration value that faithfully reflects the influence of the HCT of the blood sample on the measurement of the physical quantity.

Figure 10:
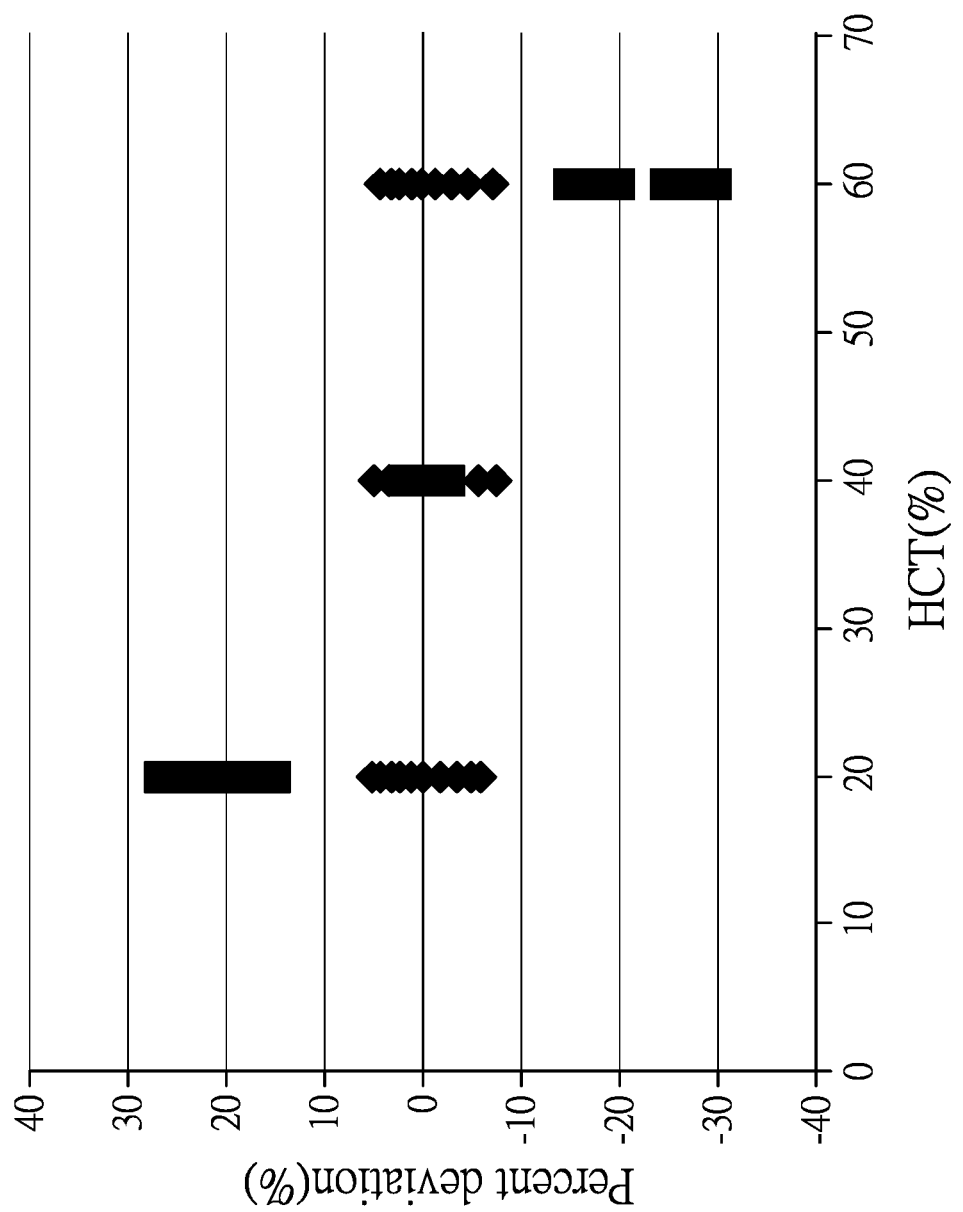
FIG. 10 is a scatter plot illustrating percent deviations of the preliminary values and the calibrated values of the blood sugar concentrations of forty five blood samples with three different HCTs in one embodiment of the method.

Referring to FIG. 10, rectangles therein represent percent deviations of the preliminary values, which correspond to the blood sugar concentrations of the blood samples before calibration in the previously mentioned nine blood sample groups, from the actual values of the blood sugar concentrations of the blood samples, and rhombuses in FIG. 10 represent percent deviations of the calibrated values, which correspond to the blood sugar concentrations of the blood samples after calibration in the previously mentioned nine blood sample groups, from the actual values of the blood sugar concentrations of the blood samples. For example, for the blood samples having the HCTs of 20%, percent deviations of the preliminary values range between 10% and 30%, and percent deviations of the calibrated values range between −10% and 10%. For the blood samples having the HCTs of 60%, percent deviations of the preliminary values range between −32% and −12%, and percent deviations of the calibrated values range between −10% and 10%. Therefore, the method of this disclosure indeed generates an accurate result of measurement of the blood sugar concentration.

Figure 11:
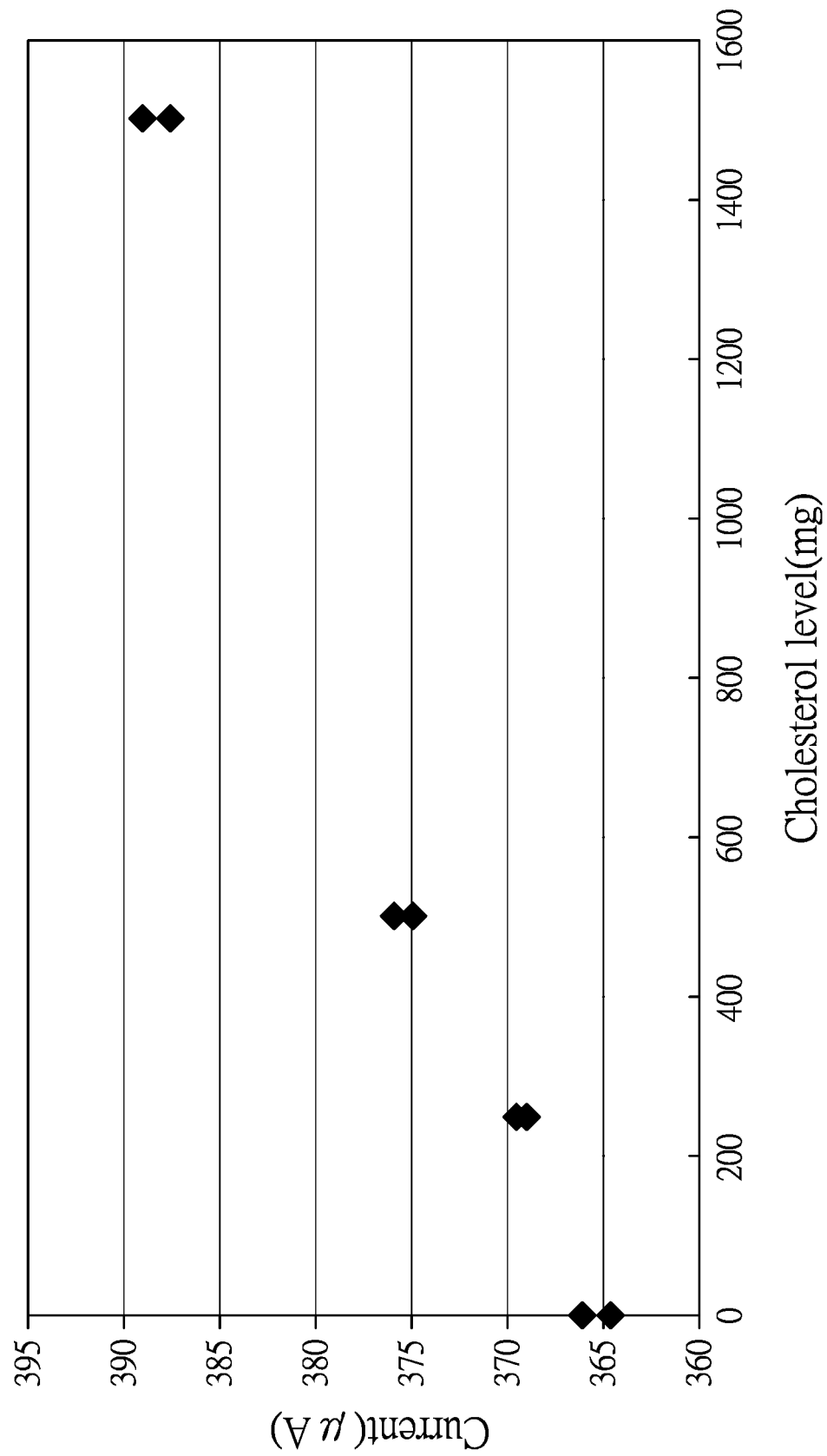
FIG. 11 is a scatter plot illustrating an example of values of electric currents that result from applying the second voltage signal on blood samples with four different cholesterol levels in one embodiment of the method and that are sampled in the fifth cycle of the pulse of the second voltage signal.

Still another experiment is given to show that the method of this disclosure is capable of generating results of measurements that reflect different cholesterol levels in the blood samples. Four blood sample groups utilized in said still another experiment correspond respectively to four different cholesterol levels (i.e., 0 mg, 250 mg, 500 mg and 1500 mg cholesterols), and each of the blood sample groups includes two samples. In other words, there are eight blood samples in total. The analyte measuring device 1 applied the first voltage signal (V1) and the second voltage signal (V2) on the blood samples, and the processor 13 read, from the sensor 12 at the time point at which the first period (P1) in the fifth cycle of the second voltage signal (V2) ends, values of electric currents resulting from the application of the second voltage signal (V2), so as to obtain eight sample points. The sample points corresponding to respective results of measurement of the electric currents are plotted in FIG. 11, where the vertical axis represents magnitude of the electric current thus measured, and the horizontal axis represents the cholesterol level of the blood sample. As shown in FIG. 11, the values of the electric currents resulting from application of the second voltage signal (V2) on the blood samples with 0 mg cholesterol are equal to about 365 µA; the values of the electric currents resulting from application of the second voltage signal (V2) on the blood samples with 250 mg cholesterols are equal to about 370 µA; the values of the electric currents resulting from application of the second voltage signal (V2) on the blood samples with 500 mg cholesterol are equal to about 375 µA; and the values of the electric currents resulting from application of the second voltage signal (V2) on the blood samples with 1500 mg cholesterol are equal to about 388 µA. That is to say, the values of the electric currents resulting from application of the first voltage signal (V1) and the second voltage signal (V2) can be utilized to determine the cholesterol levels of the blood samples. As a result, measuring the physical quantity at the time point at which the first period (P1) in the fifth one of the cycles ends helps generate the calibration value that faithfully reflects the influence of the cholesterol level of the blood sample on the magnitude of the electric currents thus measured. It is worth to note that in one embodiment, the analyte measuring device 1 generates the calibration value that is associated with the cholesterol level of the blood sample 500 based on the electric current resulting from application of the second voltage signal (V2) on the blood sample 500 (see step S4 of FIG. 2), and then calibrates the preliminary value associated with the blood sugar concentration in the blood sample 500 (see step S2 of FIG. 2) by the calibration value thus generated so as to obtain the calibrated value serving as the result of measurement of the blood sugar concentration of the blood sample 500 (see step S5 of FIG. 2).

Figure 12:
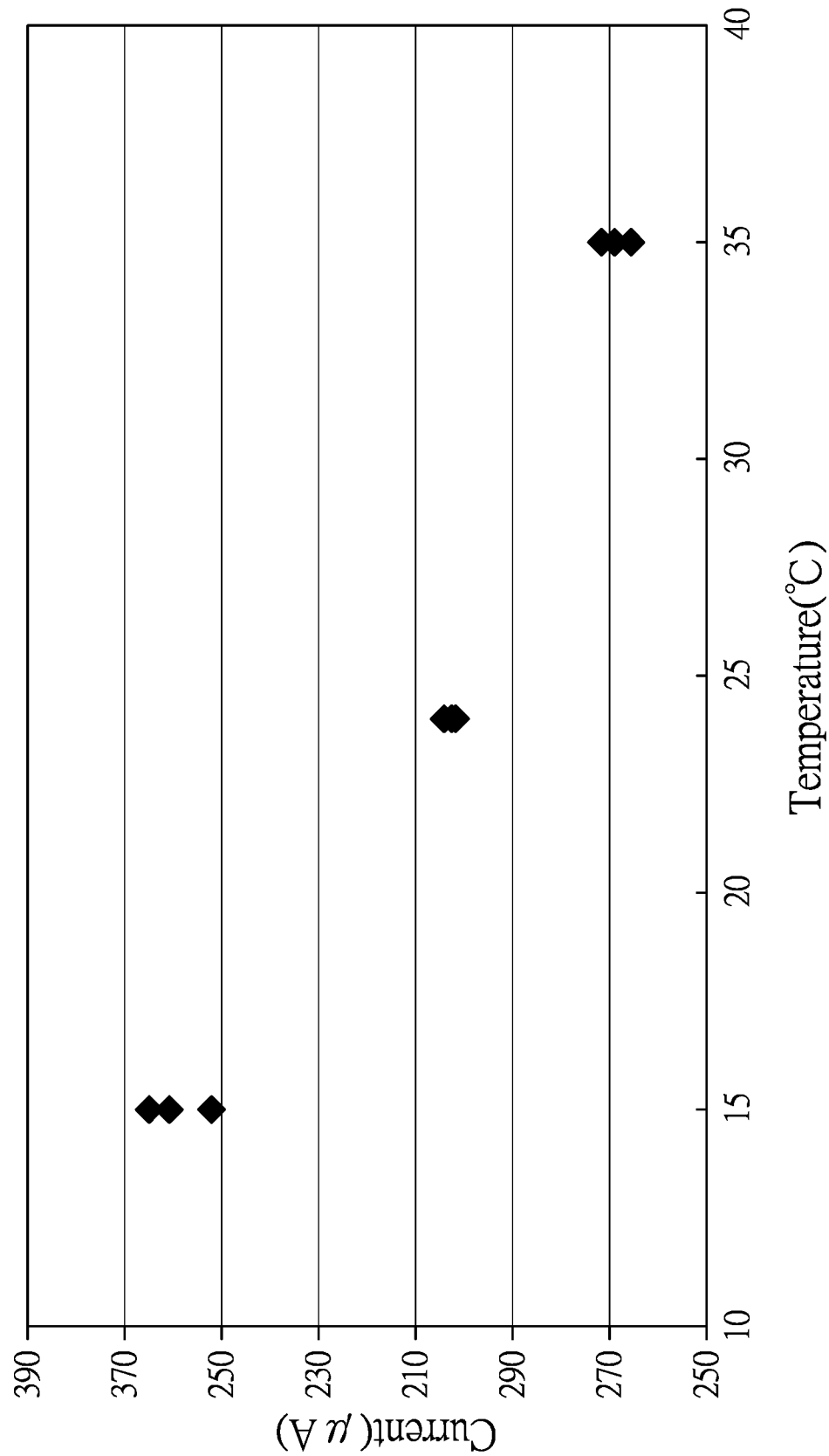
FIG. 12 a scatter plot illustrating an example of values of electric currents that result from applying the second voltage signal on blood samples under conditions of three different temperatures in one embodiment of the method and that are sampled in the fifth cycle of the pulse of the second voltage signal.

Further another experiment is given to show that the method of this disclosure is capable of generating results of measurements that reflect influences of different temperatures on the blood samples. Three blood sample groups utilized in said further another experiment correspond respectively to three temperatures (i.e., 15° C., 24° C. and 35° C.), and each of the blood sample groups includes three samples. In other words, there are nine blood samples in total. The analyte measuring device 1 applied the first voltage signal (V1) and the second voltage signal (V2) on the blood sample groups, and the processor 13 read, from the sensor 12 at the time point at which the first period (P1) in the fifth cycle of the second voltage signal (V2) ends, values of electric currents resulting from the application of the second voltage signal (V2), so as to obtain nine sample points. The sample points corresponding to respective results of measurement of the electric currents are plotted in FIG. 12, where the vertical axis represents magnitude of the electric current thus measured, and the horizontal axis represents the temperature of the blood sample. As shown in FIG. 12, the values of the electric currents resulting from application of the second voltage signal (V2) on the blood samples that were 15° C. in temperature range between 350 μA to 375 μA; values of the electric currents resulting from application of the second voltage signal (V2) on the blood samples that were 24° C. in temperature are equal to about 305 μA; and values of the electric currents resulting from application of the second voltage signal (V2) on the blood samples that were 35° C. in temperature are equal to about 270 μA. That is to say, the values of the electric currents resulting from application of the first voltage signal (V1) and the second voltage signal (V2) can be utilized to determine the temperatures of the blood samples. As a result, measuring the physical quantity at the time point at which the first period (P1) in the fifth one of the cycles ends helps generate the calibration value that faithfully reflects the influence of the temperature of the blood sample on the magnitude of the electric currents thus measured. It is worth to note that in one embodiment, the analyte measuring device 1 generates the calibration value that is associated with the temperature of the blood sample 500 based on the electric current resulting from application of the second voltage signal (V2) on the blood sample 500 (see step S4 of FIG. 2), and then calibrates the preliminary value associated with the blood sugar concentration in the blood sample 500 (see step S2 of FIG. 2) by the calibration value thus generated so as to obtain the calibrated value serving as the result of measurement of the blood sugar concentration of the blood sample 500 (see step S5 of FIG. 2).

A third embodiment of the method according to the disclosure is similar to the second embodiment of the method, but is different therefrom in the following. In the third embodiment of the method, the analyte measuring device 1 measures the physical quantity at the time point in each of P number of cycles selected from the N number of cycles of the pulse of the second voltage signal (V2) so as to generate P number of calibration values that correspond respectively to the P number of cycles, where P is an integer not smaller than two and not greater than N (e.g., N may be implemented to be five). Specifically speaking, the analyte measuring device 1 measures, for each of the P number of cycles of the pulse of the second voltage signal (V2) the physical quantity at the time point at which the first period (P1) in the cycle ends. In one embodiment, the analyte measuring device 1 measures the physical quantity at the time point in each of the five cycles (i.e., P and N are both equal to five) of the pulse of the second voltage signal (V2), so as to generate a total of five calibration values that correspond respectively to the five cycles. Subsequently, based on the calibration values, the analyte measuring device 1 calibrates the preliminary value of the analyte in the blood sample 500 so as to obtain the calibrated value of the analyte in the blood sample 500 which serves as the result of measurement of the analyte. In other embodiments, the number of measurements made in the cycles of the pulse of the second voltage signal (V2) can be implemented to be two, three or four. Even more, the number of measurements made in the cycles of the pulse of the second voltage signal (V2) can be any plural number. Results of the aforementioned measurements correspond respectively to the selected cycles of the pulse of the second voltage signal (V2). For example, when the number of measurements in the cycles of the pulse of the second voltage signal (V2) is three, three results of the measurements may correspond respectively to the first to the third cycles of the pulse of the second voltage signal (V2), or may correspond respectively to the third to the fifth cycles of the pulse of the second voltage signal (V2), or may correspond respectively to the first, the third and the fifth cycles of the pulse of the second voltage signal (V2), or may correspond respectively to the first, the second and the fourth cycles of the pulse of the second voltage signal (V2).

In one embodiment, the processor 13 of the analyte measuring device 1, based on the calibrated value, generates a notification signal that indicates the result of measurement of the analyte in the blood sample 500, and transmits the notification signal to another electronic device, such as a mobile device or a server, to inform a user of the blood sugar concentration, the cholesterol level and/or the temperature of the blood sample 500.

In summary, the method of the disclosure utilizes the analyte measuring device 1 to generate the calibration value that is associated with the HCT, the cholesterol level or the temperature of the blood sample 500, and to calibrate, based on the calibration value, the preliminary value of the blood sugar concentration of the blood sample 500 so as to obtain the calibrated value of the analyte (e.g., the blood sugar concentration) of the blood sample 500 which serves as the result of measurement of the analyte of the blood sample 500 and which is to be displayed by the display 10. To generate the calibration value, the analyte measuring device 1 measures the physical quantity (e.g., the electrical current) resulting from application of the second voltage signal (V2) including, e.g., five cycles of the pulse on the blood sample 500. In the first embodiment, the analyte measuring device 1 measures the electric current at the time point at which the first period (P1) in the fifth one of the cycles begins. In the second embodiment, the analyte measuring device 1 measures the electric current at the time point at which the first period (P1) in the fifth one of the cycles ends. In still another embodiment, the analyte measuring device 1 measures the electric current at the time point in each of five cycles of the pulse of the second voltage signal (V2). The aforementioned embodiments improve accuracy of the calibration value that is associated with the result of measurement of the electric current, and thereby enhance reliability of the result of measurement of the blood sugar concentration of the blood sample 500.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for measuring an analyte in a blood sample, to be implemented by an analyte measuring device, and comprising:

applying, by the analyte measuring device, a first voltage signal on the blood sample so as to obtain a preliminary value regarding the analyte in the blood sample based on a measured physical quantity resulting from application of the first voltage signal;

applying, by the analyte measuring device on the blood sample, a second voltage signal that includes N number of cycles of a pulse and that has a voltage value alternating between high and low levels, where N is an integer not smaller than two;

measuring, by the analyte measuring device, a physical quantity resulting from application of the second voltage signal on the blood sample at a time point in one of the cycles of the pulse of the second voltage signal so as to generate a calibration value based on the physical quantity measured at the time point; and calibrating, by the analyte measuring device based on the calibration value, the preliminary value of the analyte in the blood sample so as to obtain a calibrated value of the analyte in the blood sample which serves as a result of measurement of the analyte, wherein the measuring the physical quantity resulting from application of the second voltage signal on the blood sample at a time point includes:

measuring, by the analyte measuring device, the physical quantity at the time point in a K-th one of the cycles of the pulse of the second voltage signal, where K is an integer not smaller than two and not greater than N.

2. The method as claimed in claim 1, wherein the applying a second voltage signal includes applying, by the analyte measuring device on the blood sample, the second voltage signal that includes the N number of cycles of the pulse and that has the voltage value alternating between the high level that is positive and the low level that is negative.

3. The method as claimed in claim 2, wherein the applying a second voltage signal includes applying, by the analyte measuring device on the blood sample, the second voltage signal in which each of the cycles has a first period that corresponds to the low level that is negative, and a second period that is subsequent to the first period and that corresponds to the high level that is positive.

4. The method as claimed in claim 3, wherein the measuring the physical quantity resulting from application of the second voltage signal on the blood sample at a time point includes:

measuring, by the analyte measuring device, the physical quantity at the time point at which the first period in the K-th one of the cycles begins.

5. The method as claimed in claim 3, wherein the applying a second voltage signal includes applying, by the analyte measuring device on the blood sample, the second voltage signal in which, for each of the cycles, an absolute value of the low level corresponding to the first period in the cycle is different from an absolute value of the high level corresponding to the second period in the cycle.

6. The method as claimed in claim 3, wherein the applying a second voltage signal includes applying, by the analyte measuring device on the blood sample, the second voltage signal in which, for each of the cycles, a length of the first period in the cycle is different from a length of the second period in the cycle.

7. The method as claimed in claim 2, wherein the applying a second voltage signal includes applying, by the analyte measuring device on the blood sample, the second voltage signal in which the pulse in each of the cycles has a first period that corresponds to the high level that is positive, and a second period that is subsequent to the first period and that corresponds to the low level that is negative.

8. The method as claimed in claim 1, wherein the applying a first voltage signal includes applying, by the analyte measuring device on the blood sample, a direct current (DC) voltage signal that serves as the first voltage signal, that is positive in polarity and that has a constant voltage value.

9. A method for measuring an analyte in a blood sample, to be implemented by an analyte measuring device, and comprising:

applying, by the analyte measuring device, a first voltage signal on the blood sample so as to obtain a preliminary value regarding the analyte in the blood sample based on a measured physical quantity resulting from application of the first voltage signal;

applying, by the analyte measuring device on the blood sample, a second voltage signal that includes N number of cycles of a pulse and that has a voltage value alternating between high and low levels, where N is an integer not smaller than two;

measuring, by the analyte measuring device, a physical quantity resulting from application of the second voltage signal on the blood sample at a time point in one of the cycles of the pulse of the second voltage signal so as to generate a calibration value based on the physical quantity measured at the time point; and calibrating, by the analyte measuring device based on the calibration value, the preliminary value of the analyte in the blood sample so as to obtain a calibrated value of the analyte in the blood sample which serves as a result of measurement of the analyte, wherein the measuring the physical quantity resulting from application of the second voltage signal on the blood sample at a time point includes:

measuring, by the analyte measuring device, the physical quantity at the time point in each of P number of cycles selected from the N number of cycles of the pulse of the second voltage signal so as to generate P number of the calibration values that correspond respectively to the P number of cycles, where P is an integer not smaller than two and not greater than N.

10. The method as claimed in claim 9, wherein the applying a second voltage signal includes applying, by the analyte measuring device on the blood sample, the second voltage signal that includes the N number of cycles of the pulse and that has the voltage value alternating between the high level that is positive the low level that is negative.

11. The method as claimed in claim 10, wherein the applying a second voltage signal includes applying, by the analyte measuring device on the blood sample, the second voltage signal in which each of the cycles has a first period that corresponds to the low level that is negative, and a second period that is subsequent to the first period and that corresponds to the high level that is positive.

12. The method as claimed in claim 11, wherein the measuring the physical quantity resulting from application of the second voltage signal on the blood sample at a time point includes:
 measuring, by the analyte measuring device for each of the P number of cycles, the physical quantity at the time point at which the cycle ends.

13. The method as claimed in claim 11, wherein the applying a second voltage signal includes applying, by the analyte measuring device on the blood sample, the second voltage signal in which, for each of the cycles, an absolute value of the low level corresponding to the first period in the cycle is different from an absolute value of the high level corresponding to the second period in the cycle.

14. The method as claimed in claim 11, wherein the applying a second voltage signal includes applying, by the analyte measuring device on the blood sample, the second voltage signal in which, for each of the cycles, a length of the first period in the cycle is different from a length of the second period in the cycle.

15. The method as claimed in claim 10, wherein the applying a second voltage signal includes applying, by the analyte measuring device on the blood sample, the second voltage signal in which the pulse in each of the cycles has a first period that corresponds to the high level that is positive, and a second period that is subsequent to the first period and that corresponds to the low level that is negative.

16. The method as claimed in claim 9, where in the applying a first voltage signal includes applying, by the analyte measuring device on the blood sample, a direct current (DC) voltage signal that serves as the first voltage signal, that is positive in polarity and that has a constant voltage value.

\* \* \* \* \*